United States Patent [19]

Chan

[11] Patent Number: 5,656,635

[45] Date of Patent: Aug. 12, 1997

[54] 5-TRANS-ALCOHOLS AND THEIR USE AS OCULAR HYPOTENSIVES

[75] Inventor: Ming Fai Chan, San Diego, Calif.

[73] Assignee: Allergan, Waco, Tex.

[21] Appl. No.: 74,104

[22] Filed: Jun. 8, 1993

[51] Int. Cl.$^6$ .................. A61K 31/435; A61K 31/38; A61K 31/34; A61K 31/215

[52] U.S. Cl. .................. 514/277; 514/438; 514/464; 514/530; 514/573; 514/913; 568/838

[58] Field of Search .................. 514/530, 277, 514/573, 461, 913, 438; 568/838

[56] References Cited

U.S. PATENT DOCUMENTS 4,994,274  2/1991  Chan et al. .

OTHER PUBLICATIONS

Bito, L.Z., "Prostaglandins and Related Compounds as Potential ocular Therapeutic Agents," *Biological Protection with Prostaglandins*, Cohen, M.M., ed., Boca Raton, Fla., CRC Press, Inc., 1985, pp. 231–252.

Bito, L.Z., "Prostaglandins, Other Eicosanoids, and Their Derivatives as Potential Antiglaucoma Agents," *Applied Pharmacology in the Medical Treatment of Glaucomas* Drance, S.M. and Neufeld, A.H. eds., New York, Grune & Stratton, 1984, pp. 477–505.

Nilsson, et al., "PGF$_{2\alpha}$ Increase Uveoscleral Outflow," *Invest. Ophthalmol. Vis. Sci.* (suppl), 284, 1987.

Siebold, et al., "Esterified prostaglandin shows 'potent' promise," *Prodrug* 5 3, 1989.

Bito, L.Z., "Prostaglandins, Old Concepts and New Perspectives," *Arch. Ophthalmol.* 105, 1036, 1987.

*Primary Examiner*—Zohreh Fay
*Attorney, Agent, or Firm*—Robert J. Baran; Martin A. Voet; Howard R. Lambert

[57] ABSTRACT

The invention relates to the use of alcohol derivatives of F-type prostaglandins as ocular hypotensives. The PGF derivatives used in accordance with the invention are encompassed by the following structure formula I:

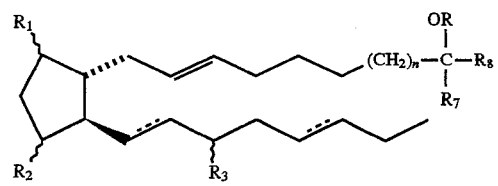

wherein wavy line attachments indicate either the alpha ($\alpha$) or beta ($\beta$) configuration; hatched lined indicate $\alpha$ configuration, solid triangles are used to indicate $\beta$ configuration, dashed bonds represent a double bond, or a single bond; n is 0, or an integer of from 1 to 3; R is hydrogen or a —(CO)R$_4$ group; R$_1$, R$_2$, and R$_3$ independently are hydroxyl, or —O(CO)R$_5$ groups, wherein R$_4$ and R$_5$ independently stand for saturated or unsaturated acyclic hydrocarbon having from 1 to 20 carbon atoms, or —(CH$_2$)$_m$R$_6$ where m is 0–10 and R$_6$ is an aliphatic, aromatic or heteroaromatic ring. R$_7$ and R$_8$ independently are hydrogen or alkyl of 1 to 6 carbon atoms or pharmaceutically acceptable salts thereof.

11 Claims, No Drawings

5-TRANS-ALCOHOLS AND THEIR USE AS OCULAR HYPOTENSIVES

FIELD OF THE INVENTION

The present invention relates to 5-trans-prostaglandin alcohols of the F series and their esters. More particularly, the present invention concerns 5-trans prostaglandin F (PGF) alcohols and esters, that are potent ocular hypotensives, and are particularly suitable for the management of glaucoma.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

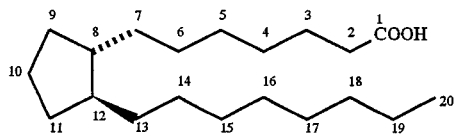

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by $\alpha$ or $\beta$ [[e.g. prostaglandin $F_{2\alpha}$ ($PGF_{2\alpha}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et.al., *Prodrug* 53 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed 27 Jul. 1989), relates to certain 11-acyl-prostaglandins, such as 11-pivaloyl, 11-acetyl, 11-isobutryryl, 11-valeryl, and 11-isovaleryl $PGF_{2\alpha}$. Intraocular pressure reducing 15-acyl prostaglandins are disclosed in the co-pending application U.S. Ser. No. 357,394 (filed 25 May 1989). Similarly, 11,15-9,15 and 9,11-diesters of prostaglandins, for example 11,15-dipivaloyl $PGF_{2\alpha}$ are known to have ocular hypotensive activity. See the co-pending patent applications U.S. Ser. Nos. 385,645, 386,312 and 386,834 (all filed 27 Jul. 1989). The disclosures of all of these patent applications are hereby expressly incorporated by reference.

SUMMARY OF THE INVENTION

The present invention concerns a method of treating ocular hypertension which comprises administering to a mammal having ocular hypertension a therapeutically effective amount of a compound of formula I:

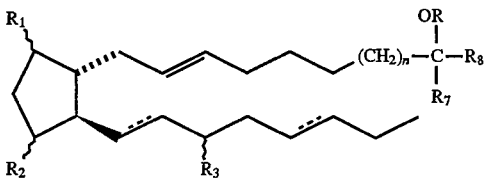

wherein wavy line attachments indicate either the alpha (α) or beta (β) configuration; hatched lines indicate α configuration, solid triangles are used to indicate β configuration, dashed bonds represent a double bond or a single bond, n is 0 or an integer of from 1 to 3; R is hydrogen or a —(CO)$R_4$ group; $R_1$, $R_2$, and $R_3$ independently are hydroxyl, or —O(CO)$R_5$ groups, wherein $R_4$ and $R_5$ independently stand for saturated or unsaturated acyclic hydrocarbons having from 1 to 20 carbon atoms, or —(CH$_2$)$_m$R$_6$ where m is 0–10 and $R_6$ is an aliphatic, aromatic or heteroaromatic ring, $R_7$ and $R_8$ independently are hydrogen or alkyl of 1 to 6 carbon atoms, or a pharmaceutically acceptable salt thereof.

In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable liquid vehicle, packaged in a container suitable for metered application.

In a still further aspect, the present invention relates to a pharmaceutical product, comprising a container adapted to dispense its contents in a metered form; and an ophthalmic solution therein, as hereinabove defined.

DETAILED DESCRIPTION OF THE INVENTION

The present invention relates to the use of alcohol derivatives of F-type prostaglandins as ocular hypotensives. The PGF derivatives used in accordance with the present invention are encompassed by the following structural formula I:

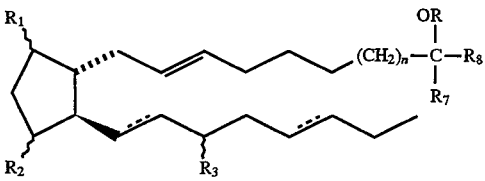

wherein the substituents and symbols are as hereinabove defined. The dotted lines on bonds between carbons 13 and 14 (C-13) and carbons 17 and 18 (C-17) indicate a single or double bond. If two solid lines are used at C-13, or C-17, it indicates a specific configuration for that double bond. Hatched lines used at position C-9, C-11 and C-15 indicate the α configuration. If one were to draw the β configuration, a solid triangular line would be used at either of these three positions.

A preferred group of the compounds of the present invention includes PGF$_{2\alpha}$ derivatives that have the following structural formula II:

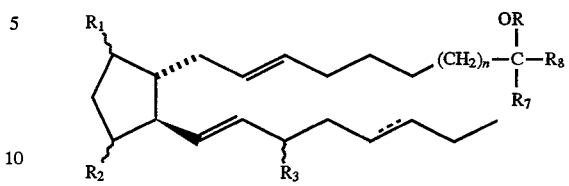

Another preferred group includes PGF$_{3\alpha}$ derivatives having the formula III:

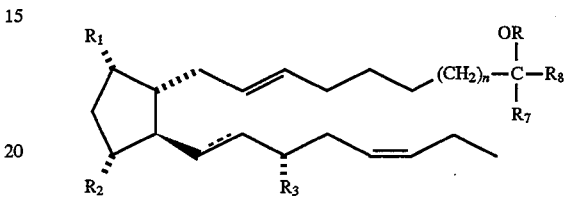

In the above formulae, the substituents and symbols are as hereinabove defined.

The compounds and esters of the present invention may be prepared by methods that are known in the art. The primary alcohols can be conveniently prepared by reduction of the 1-carboxyl group of the corresponding PGF compounds. For example, in an analogous process the reduction of PGF$_{2\alpha}$ methyl ester with diisobutylaluminium hydride in either at 25° C. is disclosed by Maddox et.al., Nature 273, 549 (1978).

In general, the reduction may be performed by chemical reducing agents conventionally used for the conversion of carboxylic acids to alcohols. Chemical reducing agents include, but are not restricted to hydrides, such as lithiumaluminium hydride or diisobutylaluminium hydride. As an alternative to direct reduction, the PGF acid may be converted into a corresponding 1-ester before reduction, and the obtained 1-ester may be reduced by chemical reduction. Methods of esterification and reduction of PGF compounds are disclosed in the Example below.

The hydroxyl group(s) present in any of the positions 9, 11 and 15 are protected from reduction by protecting groups known in the art.

The secondary and tertiary alcohols are usually prepared from the corresponding primary alcohols via oxidation to aldehydes or ketones and subsequent reaction with a suitable Grignard reagent. These reactions are well known in organic chemistry.

Esterification of the PGF 1-alcohols of this invention may further increase the ocular hypotensive activity, therefore, the compounds of formula (I) in which R is other than hydrogen are within the scope of the present invention.

In a preferred group of the PGF compounds of formula (I) the hydroxyl groups in the 9, 11 and/or 15 positions are esterified. Particularly preferred are the 11-esters, 15-esters, 11,15-, 9,15- and 9,11-diesters. Esterification in these positions may be performed after the reduction of the 1-carboxyl group with appropriate protection.

The prostaglandin esters according to the present invention can comprise a variety of acyl substituents. In formula (I) $R_4$ and $R_5$ as acyclic hydrocarbons having from one to twenty carbon atoms, inclusive, preferably are straight or branched-chain alkyl, alkenyl or alkynyl groups of one to ten carbon atoms, such as methyl, ethyl, propyl, butyl, pentyl, etc., or an isomeric form thereof; vinyl, propenyl, etc. Most preferably, $R_4$ and/or $R_5$ are —$CH_3$, —$(CH_2)_3CH_3$, —$CH(CH_3)_2$ or —$C(CH_3)_3$.

Alternatively, $R_4$ and $R_5$ can comprise a cyclic component ($R_6$), which preferably is a saturated or unsaturated ring having from three to seven carbon atoms; or an aromatic or heteroaromatic ring, preferably having 5 to 10 carbon atoms and containing oxygen, nitrogen or sulfur as a heteroatom, if present. That is, $R_6$ may be phenyl, thienyl, pyridyl, or furyl, or the mono or disubstituted halo, e.g., fluoro or chloro, or $C_1$ to $C_3$ alkyl derivatives, thereof. Preferably, m is an integer between 0 and 4.

In another preferred group of the compounds of Formula (I) $R_7$ and $R_8$ are both hydrogen, or $R_7$ is hydrogen and $R_8$ is alkyl of one to six, preferably one to four carbon atoms.

A pharmaceutically acceptable salt is any salt which retains the activity of the parent compound and does not impart any deleterious or undesirable effect on the subject to whom it is administered and in the context in which it is administered. Of particular interest are salts formed with inorganic ions, such as sodium, potassium, calcium, magnesium and zinc.

Pharmaceutical compositions may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001–5. |
| preservative | 0–0.10 |
| vehicle | 0–40 |
| tonicity adjustor | 1–10 |
| buffer | 0.01–10 |
| pH adjuster | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

The invention is further illustrated by the following non-limiting Examples.

EXAMPLE 1

Preparation of 1-Decarboxyl-1-hydroxymethyl-5-trans prostaglandin $F_{2\alpha}$

A solution of diazomethane in ether was added dropwise to a solution of 5-trans $PGF_{2\alpha}$ (obtained from Cayman Chemical Company, 10 mg) in 1.5 ml methanol at 0° C. until a yellow color persisted. The solution was stirred at 0° C. for a further 10 minutes and the solvents were evaporated under reduced pressure to obtain 10.7 mg of 5-trans $PGF_{2\alpha}$ methyl ester as a colorless semi-solid.

$^1$H NMR (CDCL$_3$, 300 MHz): δ5.56 (1H, ½ ABX, $J_{AB}$=15.2, $J_{AX}$=6.7 Hz), 5.4–5.5 (3H, m), 4.20 (1H, t, J=4 Hz), 4.06 (1H, q, J=6.6 Hz), 3.96 (1H, m), 3.67 (3H, s, methyl ester), 2.30 (2H, t J=7.5 Hz), 2.0–2.6 (9H, m), 1.2–1.8 (12H, m) and 0.89 ppm (3H, t J=6.7 Hz).

The crude ester above was dissolved in dry tetrahydrofuran (THF, 1 ml) and cooled to −78° C. in a dry ice-acetone bath. A solution of diisobutylaluminum hydride in methylene chloride (1.0M, 0.23 ml) was added. The dry ice-acetone bath was replaced with an ice bath after 15 minutes and stirring was continued for 2.5 hours at 0° C. Methanol (0.25 ml) was added to destroy excess diisobutylaluminum hydride. The crude reaction mixture was diluted with 10% citric acid solution and extracted with 4×8 ml ethyl acetate. The combined organic extracts were washed with saturated sodium carbonate and brine, dried over magnesium sulfate and concentrated to give 8 mg. crude product. Purification was achieved by column chromatography over silica gel using gradient elution (ethyl acetate to 5% methanol in ethyl acetate) giving 6.0 mg. pure 1-decarboxyl-1-hydroxymethyl-5-trans prostaglandin $F_{2\alpha}$ (62% yield overall).

$^1$H NMR (300 MHz, CDCL$_3$): δ5.55 (1H, ½ ABX, $J_{AB}$=15.3, $J_{AX}$=6.9 Hz, H-14), 5.4–5.5 (3H, m), 4.19 (1H, distorted t, J=4 Hz), 4.05 (1H, q, J=6.6 Hz), 3.85–3.95 (1H, m), 3.63 (2H, t, J=6.5 Hz, C$\underline{H}_2$OH), 3.2 (1H, br s), 2.5 (2H, br s), 1.8–2.4 (7H, m) 1.73 (1H, ½ ABX, $J_{AB}$=15, $J_{AX}$=2.8 Hz), 1.2–1.6 (13H, m) and 0.89 ppm (3H, distorted t, J=7 Hz);

$^{13}$C NMR (75 MHz, CDCL$_3$): δ13.78 (CH$_3$), 22.41 (CH$_2$), 25.02 (CH$_2$), 25.31 (CH$_2$), 30.95 (CH$_2$), 31.54 (CH$_2$), 31.91 (CH$_2$), 32.02 (CH$_2$), 37.12 (CH$_2$), 42.50 (CH$_2$), 49.85 (CH), 55.55 (CH), 62.67 (CH$_2$), 73.01 (CH), 77.20 (CH), 78.04 (CH), 129.17 (CH), 131.70 (CH), 132.75 (CH) and 135.37 (CH) ppm;

IR (CHCl$_3$): 3200–3600, 1225, 1130, 1100, 970 and 928 cm$^{-1}$.

MS (EI, TMS derivative): m/z 628 (M$^+$, 0.2%), 217 (26%), 191 (100%), 173 (73%), 129 (46%), 73 (60%).

HRMS (EI, TMS derivative): calculated for C$_{32}$H$_{68}$O$_4$Si$_4$: 628.4163, found: 628.4179.

EXAMPLE 2

Intraocular Pressure Reducing Activity

Experimental quantities of the compound of Example 1 are prepared in an ophthalmic formulation containing 0.1% polysorbate (Tween 80)—10 mM TRIS. One eye of each experimental animal is treated by applying one 25 ul drop of the drug formulation to the ocular surface, the contralateral eye received 25 ul of vehicle as a control. Intraocular pressure is measured by applanation pneumatonometry immediately before drug administration and at subsequent, predetermined times thereafter. Rabbits, dogs and cynomolgus monkeys are employed as experimental animals. The data shows that the compound of Example 1 has ocular hypotensive activity.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

I claim:

1. A method of treating ocular hypertension which comprises administering to a mammal having ocular hypertension a therapeutically effective amount of a compound of formula I:

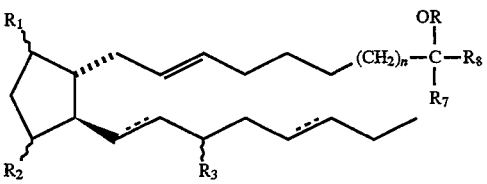

wherein wavy line attachments indicate either the alpha (α) or beta (β) configuration; hatched lines indicate α configuration, solid triangles are used to indicate β configuration, dashed bonds represent a double bond, or a single bond; n is 0 or an integer of from 1 to 3; R is hydrogen or a —(CO)R$_4$ group; R$_1$, R$_2$ and R$_3$ independently are hydroxyl, or —O(CO)R$_5$ groups, wherein R$_4$ and R$_5$ independently stand for saturated or unsaturated acyclic hydrocarbon having from 1 to 20 carbon atoms, or —(CH$_2$)$_m$R$_6$ where m is 0–10 and R$_6$ is an aliphatic, aromatic or heteroaromatic ring, wherein said heteroaromatic ring is selected from the group consisting of thienyl, pyridyl and furyl and the mono or disubstituted halo or C$_1$ to C$_3$ alkyl derivatives thereof R$_7$ and R$_8$ independently are hydrogen or alkyl of 1 to 6 carbon atoms or pharmaceutically acceptable salts thereof.

2. The method of claim 1 wherein said compound of formula I is selected from the group consisting of PGF$_{2\alpha}$ and PGF$_{3\alpha}$ derivatives.

3. The method of claim 2 wherein R is hydrogen.

4. The method of claim 3 wherein R$_7$ and R$_8$ each is hydrogen.

5. The method of claim 3 wherein R$_7$ is hydrogen and R$_8$ is alkyl of one to 6 carbon atoms.

6. The method of claim 5 wherein R$_7$ is hydrogen and R$_8$ is alkyl of one to 4 carbon atoms.

7. The method of claim 2 wherein R is —(CO)R$_4$, in which R$_4$ is —C(CH$_3$)$_3$.

8. The method of claim 2 wherein said compound of formula I is 1-decarboxyl-1-hydroxy-methyl-5-trans prostaglandin F$_{2\alpha}$ and pharmaceutically acceptable salts.

9. An ophthalmic solution comprising a therapeutically effective amount of a compound of formula I, as defined in claim 1, or a pharmaceutically, acceptable salt thereof, in admixture with a non-toxic, ophthalmically acceptable liquid vehicle, packaged in a container suitable for metered application.

10. A pharmaceutical product, comprising a container adapted to dispense to contents of said container in metered form; and an ophthalmic solution in said container comprising a compound of formula I as defined in claim 1, or a pharmaceutically acceptable salt thereof, in admixture with a non-toxic, ophthalmically acceptable liquid vehicle.

11. 1-decarboxyl-1-hydroxymethyl-5-trans prostaglandin F$_{2\alpha}$.

* * * * *

UNITED STATES PATENT AND TRADEMARK OFFICE
CERTIFICATE OF CORRECTION

PATENT NO. : 5,656,635
DATED : August 12, 1997
INVENTOR(S) : Chan

It is certified that error appears in the above-indentified patent and that said Letters Patent is hereby corrected as shown below:

Column 6, line 65; delete " δ85.55" and insert in place thereof -- δ5.55--

Signed and Sealed this

Twenty-third Day of December, 1997

Attest:

BRUCE LEHMAN

Attesting Officer

Commissioner of Patents and Trademarks